United States Patent [19]
Noguchi et al.

[11] Patent Number: 5,304,471
[45] Date of Patent: Apr. 19, 1994

[54] PROCESS FOR PRODUCING FOREIGN PROTEIN IN *ESCHERICHIA COLI*

[75] Inventors: Toshitada Noguchi, Choshi; Hideo Takahashi, Nagareyama, both of Japan

[73] Assignee: Yamasa Shoyu Kabushiki Kaisha, Chiba, Japan

[21] Appl. No.: 653,225

[22] Filed: Feb. 8, 1991

[30] Foreign Application Priority Data

Feb. 9, 1990 [JP] Japan .................................... 2-31123

[51] Int. Cl.⁵ .................... C12P 21/02; C12N 7/01; C12N 15/70; C12N 15/00
[52] U.S. Cl. .................. 435/69.1; 435/235.1; 435/320.1; 935/31; 935/38
[58] Field of Search .................. 435/69.1, 71.1, 71.2, 435/172.1, 252.3, 320.1, 948; 935/22, 31, 33, 38, 73

[56] References Cited

U.S. PATENT DOCUMENTS 4,845,031  7/1989  Shub et al. ........................ 435/69.1

FOREIGN PATENT DOCUMENTS 0133044  2/1985  European Pat. Off. .

OTHER PUBLICATIONS

Shub et al., "Bacteriophage T4, a New Vector for the Expression of Cloned Genes", Gene, 37:31–36, (1985).
Noguchi et al., Chemical Abstracts, vol. 105, 1986, Abstract No. 220261, (JP 61, 162, 168; Jul. 1986).
Duvoisin et al., Gene, vol. 45, (1986), pp. 193–201.
Snyder et al., Pro. Natl. Acad. Sci. U.S.A., vol. 73, No. 9, pp. 3098–3102.

*Primary Examiner*—Richard A. Schwartz
*Assistant Examiner*—James Ketter
*Attorney, Agent, or Firm*—Wenderoth, Lind & Ponack

[57] ABSTRACT

A process of producing a foreign protein is provided which comprises transforming *E. coli* with a plasmid carrying a fused DNA having a DNA fragment encoding a foreign protein located downstream of a transcription initiation signal and translation initiation signal both derived from an appropriate T4 phage gene, infecting the transformant with a T4 phase denB and/or alc mutant at a low multiplicity of infection, and then culturing the infected transformant. The desired foreign protein can be produced in an extremely high yield, as compared to the prior art technique.

5 Claims, 1 Drawing Sheet

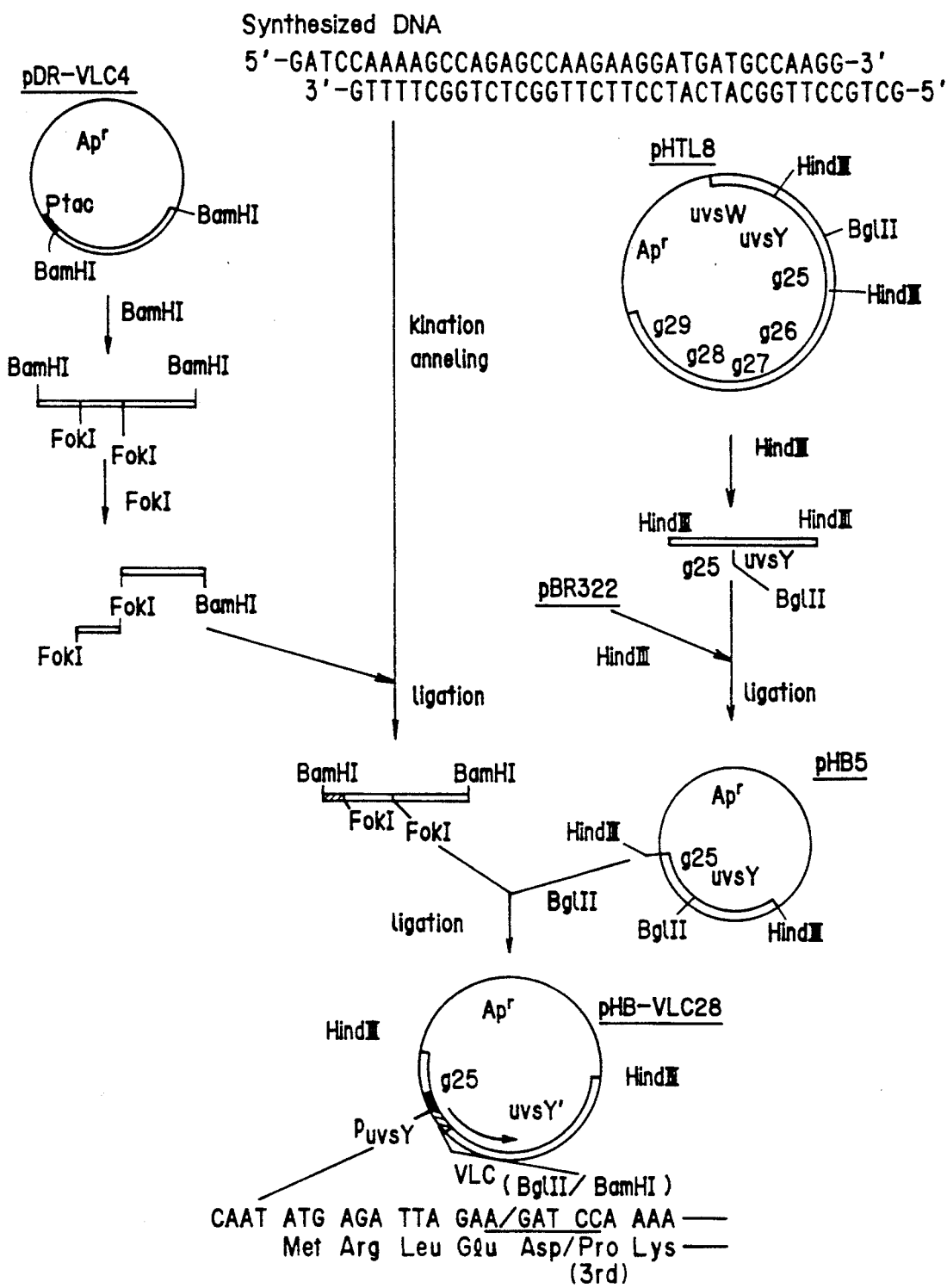

5,304,471

SEQUENCE LISTING ( 1 ) GENERAL INFORMATION:

(  i i i ) NUMBER OF SEQUENCES: 3

( 2 ) INFORMATION FOR SEQ ID NO:1:

( i ) SEQUENCE CHARACTERISTICS:
        ( A ) LENGTH: 37 base pairs
        ( B ) TYPE: Nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANISM:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

GATCCAAAAG CCAGAGCCAA GAAGGATGAT GCCAAGG      37

( 2 ) INFORMATION FOR SEQ ID NO:2:

( i ) SEQUENCE CHARACTERISTICS:
        ( A ) LENGTH: 37 base pairs
        ( B ) TYPE: Nucleic acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:

(B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANISM:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:2:

GCTGCCTTGG CATCATCCTT CTTGGCTCTG GCTTTTG                37

(2) INFORMATION FOR SEQ ID NO:3:

(i) SEQUENCE CHARACTERISTICS:
                (A) LENGTH: 4 amino acid residues
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANISM:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:

(D) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:3:

Arg Leu Glu Asp
1

PROCESS FOR PRODUCING FOREIGN PROTEIN IN ESCHERICHIA COLI

BACKGROUND OF THE INVENTION

1. Field of the Invention

The present invention relates to a process for producing a foreign protein in *Escherichia coli* as a host by recombinant DNA technique.

2. Related Prior Art Statement

Where a foreign protein is produced in *E. coli* by recombinant DNA technique, some foreign proteins are highly sensitive to proteases in *E. coli* and their productivity is therefore extremely poor in an ordinary expression system. Even if a foreign protein is not highly sensitive to protease in *E. coli*, many proteins are somehow affected by proteases so that their yield decreases.

T4 phage is one of the known virulent phages, a host of which is *E. coli*, and it has an excellent ability of producing, e.g., an inhibitor on host protease(s) which are involved in degradation of abnormal proteins [Simon et al., Nature, 275, 424 (1978)]. For this reason, it is extremely beneficial from an industrial viewpoint to apply various functions of T4 phage, especially the ability to produce an inhibitor on host protease(s) to the production of useful substances by recombinant DNA technique using *E. coli* as a host.

For the purpose of directly utilizing the functions of T4 phage, research has been heretofore conducted to clone a DNA fragment encoding a foreign protein to the T4 phage genome to convert the T4 phage itself into an expression vector [Casna et al., Gene, 18, 297 (1982), Noguchi et al., Gene, 44, 133 (1986), Mattson et al., Japanese National Publication No. 60-502187]. All of this research utilizes the DNA recombination activity of T4 phage, based on the replacement by DNA recombination in vivo of T4 phage DNA cloned in a plasmid with the genome of T4 phage infected to a host due to their DNA homology, thereby to introduce the DNA fragment encoding a foreign protein into phage genome. According to this technique, a suitable T4 phage promoter ligated with the gene encoding a foreign protein to be expressed can be introduced the phage genome, thus at least succeeding to render the T4 phage itself an expression vector [Casna et al., Gene, 37, 31 (1985), Noguchi et al., Japanese Patent Application Laid-Open No. 62-232384].

T4 phage carries hydroxymethylcytosine (HMC), which is an abnormal base, in its DNA strand instead of normal cytosine (C). When mutations are introduced into genes 42, 56, denB and alc, however, the HMC is completely substituted with normal C [Snyder et al., Proc. Natl. Acad. Sci. (USA), 73, 2098 (1976)]. Such a multiple mutant is generally called T4dC phage. Since T4dC phage is deficient in denB gene(endonuclease IV-deficient), the phage has an extremely high frequency of DNA recombination with a plasmid as compared to a wild type phage. Therefore, in the prior art technique, after the infection of T4dC phage, DNA recombination with a plasmid is caused to construct recombinant T4dC phage [Noguchi et al., Gene, 44, 133 (1986)]. However, T4dC phage is a multiple mutant so that its proliferation ability is poor as compared to a wild type phage and its productivity of an expressed product also decreases. In order to express the desired foreign protein in a high quantity, in the prior art technique it was thus necessary to construct HMC recombinant phage by further hybridization of the recombinant T4dC phage with a wild type phage.

As stated above, it was very complicated to render T4 phage itself an expression vector, including preparation of a hybrid plasmid. Furthermore, an amount of the desired foreign protein to be expressed was not sufficiently satisfactory [Noguchi et al., Japanese Patent Application Laid-Open No. 62-232384, Casna et al., Gene, 37, 31 (1986)].

SUMMARY OF THE INVENTION

The present inventors have made various investigations to develop a simpler process unlike the prior art technique involving conversion of T4 phage itself into an expression vector and as a result, have found that by infecting T4 phage denB and/or alc mutant at a low m.o.i. (multiplicity of infection) to *E. coli* transformed with a plasmid carrying a fused DNA having a DNA fragment encoding a desired foreign protein to be expressed downstream of a transcription initiation signal and a translation initiation signal derived from an appropriate T4 gene, the desired foreign protein can be produced in an extremely high yield, as compared to the prior art technique. The present invention has thus been accomplished.

That is, the present invention is directed to a process for producing a foreign protein in *Escherichia coli* comprising the steps of:

(A) ligating operably a DNA fragment encoding the foreign protein downstream of a transcription initiation signal and a translation initiation signal both derived from a T4 phage gene and inserting the resulting DNA fragment into a plasmid replicable in *E. coli* to construct a hybrid plasmid;

(B) transforming *E. coli* with the hybrid plasmid obtained in step A;

(C) proliferating the transformant obtained in step B in a medium in which said transformant can proliferate and infecting the transformant with a T4 phage denB and/or alc mutant at a low multiplicity of infection (m.o.i.);

(D) culturing the phage-infected transformant obtained in step C to express the foreign protein; and, (E) recovering the cultured transformants in step D to harvest the desired foreign protein.

BRIEF DESCRIPTION OF THE DRAWING

FIG. 1 shows construction of pHB-VLC28.

DESCRIPTION OF THE PREFERRED EMBODIMENTS

In the specification, the following terms are used to mean as defined below.

The term "transcription initiation signal and translation initiation signal" refers to a DNA fragment containing a specific nucleotide sequence required for transcription from template DNA to messenger RNA (mRNA) and translation of information on mRNA into a protein. The nucleotide sequences of DNAs corresponding to the transcription initiation signal and translation initiation signal in T4 phage and in *E. coli*, which is a host of T4 phage, are somewhat different from each other [Rabussay, in "Bacteriophage T4", edited by Mathews et al., American Society for Microbiology, Washington, D.C., 167–173 (1983)]. After the infection of T4 phage, the host gene expression is therefore completely shut off and only the phage gene is expressed. For this reason, those derived from T4 phage gene or synthetic DNA fragments having the same function as in those derived from T4 phage gene are used in the process of the present invention as the transcription initiation signal and translation initiation signal. Specific examples of genes containing the transcription initiation signal and translation initiation signal derived from T4 phage gene which can be used in the present invention include an early or middle T4 phage gene such as uvsY gene and a late T4 phage gene such as gene 18 and gene 22.

The term "DNA fragment encoding a foreign protein" refers to a DNA fragment encoding a protein or peptide used for the purpose of producing a desired substance. The DNA fragment encoding a foreign protein which can be used in the process of the present invention is not restricted to its kind, origin, source, or the like and may be any one of DNA fragments obtained from natural matters such as animals, plants, microorganisms, etc.; DNA fragments obtained by acting a reverse transcriptase, etc. on mRNAs obtained from the natural matters described above; chemically synthesized DNA fragments, and the like.

The term "plasmid" refers to a plasmid having a site which will be cleaved with a specific restriction enzyme and capable of replicating in $E.$ $coli.$ In the process of the present invention, any plasmid can be used so long as it meets the requirements described above. In order to enhance an amount of the desired protein or peptide produced, it is desired to use a plasmid having a high copy number in the cells. Preferred examples are plasmids of ColE1 type, pMB9 type, pBR322 type, pSC101 type, R6K type, etc. Specific examples include pBR322 [Boliver et al., Gene, 2, 95 (1975)], pUC18, pUC19 [Messing et al., Methods in Enzymology, 101, 20 (1983)], etc.

The term "m.o.i." (multiplicity of infection) refers to the number of phage infected per cell.

The process of the present invention is characterized by the following steps (A) through (E).

(A) step of ligating operably a DNA fragment encoding the foreign protein downstream of a transcription initiation signal and a translation initiation signal both derived from a T4 phage gene and inserting the resulting DNA fragment into a plasmid replicable in $E.$ $coli$ to construct a hybrid plasmid;

(B) step of transforming $E.$ $coli$ with the hybrid plasmid obtained in step A;

(C) step of proliferating the transformant obtained in step B in a medium in which said transformant can proliferate and infecting the transformant with a T4 phage denB and/or alc mutant at a low multiplicity of infection (m.o.i.);

(D) step of culturing the phage-infected transformant obtained in step C to express the foreign protein; and, (E) step of recovering the cultured transformants in step D to harvest the desired foreign protein.

I. Step A

A technique for ligation of a DNA fragment containing the transcription initiation signal and translation initiation signal derived from T4 phage gene and a DNA fragment encoding the foreign protein and a technique for inserting the fused DNA into a plasmid in step A are well known to the skilled in the art, especially, in the fields of biochemistry, molecular biology and genetic engineering. More specifically, these procedures may be carried out according to the methods described in, e.g., "Molecular Cloning" [edited by Maniatis et al., Cold Spring Harbor, Cold Spring Harbor Laboratory, New York (1982)].

II. Step B $E.$ $coli$ used in step B is not particularly limited to the kind of its strain as long as it is highly safe and easily handled. Where T4dC phage is used to infect, however, a restriction-deficient strain is desirable as $E.$ $coli$ strain. More specifically, there may be used JM105, JM109 [Messing et al., Methods in Enzymology, 101, 20 (1983)], MC1061 [Casadaban and Cohen, $J.$ $Mol.$ $Biol.,$ 138, 179 (1980)], etc. which are often used in recombinant DNA experiments.

For transformation of $E.$ $coli$, there may be used a conventional manner such as treatment of $E.$ $coli$ with calcium chloride at a low temperature to transduce a plasmid into the cells [Mandel et al., $J.$ $Mol.$ $Biol.,$ 53, 159 (1970)], etc.

III. Step C

The transformant may be cultured in a medium containing nutrient sources required for proliferation of $E.$ $coli$ such as carbon sources, nitrogen sources, etc. in a conventional manner. Using a medium as used for culturing $E.$ $coli$ such as 2xYT medium [Messing et al., Methods in Enzymology, 100, 20 (1983)], LB medium, M9CA medium (edited by Maniatis et al., Molecular Cloning, supra), etc., which is supplemented with chemicals, e.g., an appropriate antibiotic (ampicillin, tetracycline, etc.) to prevent the falling off of plasmid, etc., the transformant may be cultured at 20° to 40° C., if necessary and desired, with aeration and under stirring.

In order to induce expression of the foreign protein, the transformant is infected with T4 denB and/or alc mutant at a low m.o.i., preferably in a range from 0.01 to 1.0. As the T4 phage mutant to be used for the infection, where the desired foreign gene is expressed at the early stage or middle stage of T4 phage development using the transcription initiation signal and translation initiation signal derived from an early or middle T4 phage gene, it is preferable to use T4 alc mutant. In the infection of alc+ phage, transcription from plasmid DNA containing normal cytosine is inhibited [Snyder, L., et al., Proc. Natl. Acad. Sci. USA, 73, 2093 (1976), Kutter, E. M., et al., J. Virol., 40, 822 (1981)]. On the other hand, where the foreign gene is expressed at the later stage of phage development using the transcription initiation signal and translation initiation signal derived from a T4 late gene, it is desired to use T4 denB− mutant. The denB gene is expressed at the early denB− stage of infection and its product degrades DNA containing normal cytosine [Warner, H. R. and Snustad, D. P., Bacteriophage T4, edited by Mathews, C. K., et al., American Society for Microbiology, Washington, D.C., 1983, pp. 103–109]. Therefore, in the infection of denB+ phage, expression from the T4 late promoter in plasmid at the later stage of infection is extremely decreased. Recombination occurs between plasmid carrying transcription initiation signal and translation initiation signal derived from the late T4 phage gene and infected phage genome due to their homology and the plasmid is replicated as DNA containing HMC [Mattson, T., et al., J. Mol. Biol., 170, 357 (1983)] so that alc mutation is unnecessary in this case. From a standpoint of productivity, however, it is preferred to use both denB and alc genes-mutated phage (denB and alc mutant). Specific examples include T4dC phage which has mutation in genes denB and alc, and the like. Further for enhancing the productivity of the foreign protein, it may be effective to utilize lysis inhibition phenomenon ("Experimental Method for Bacteriophage", Junichi Tominaga, May 30, 1970, published by Iwanami Publishing Co.); in this case, it is preferred to use rII+ phage.

IV. Step D

Even after the phage infection, the cultivation of the transformant is conducted for several hours. Specifically, the phage-infected bacteria may be cultured at the temperature of 20° to 40° C. for about 0.5 to about 10 hours. It is also desired to culture with sufficient aeration and under stirring.

V. Step E

After the cultivation, the desired protein may be harvested from the cells by suitably applying a conventional manner. For example, the recovered cells are suspended in an appropriate buffer, the cells are disrupted in a conventional manner such as ultrasonic oscillation, etc. and the desired protein is extracted. After the cell debris is removed by centrifugation, the desired protein may be purified by ion exchange chromatography, gel filtration, etc.

The process of the present invention comprises ligating operably the DNA fragment encoding the foreign protein downstream of the transcription initiation signal and translation initiation signal derived from an appropriate T4 phage gene, without the necessity of rendering T4 phage itself an expression vector as required in the prior art, and inserting the ligated DNA fragment into a plasmid replicable in *E. coli* to construct a hybrid plasmid (step A), transforming *E. coli* with the hybrid plasmid (step B), infecting the transformant with T4 phage denB and/or alc mutant at a low m.o.i. (step C) and expressing and recovering the desired foreign protein (steps D and E). In such an extremely simple manner, the foreign protein sensitive especially to *E. coli* protease, which had a poor productivity in *E. coli* according to conventional methods, can be produced in *E. coli* in a high quantity, utilizing T4 phage capable of producing a protease inhibitor. In addition, the expression system used in the process of the present invention can be constructed extremely easily and can enhance the productivity of the foreign protein due to infection of T4 phage denB and/or alc mutant at a low m.o.i.

That is, the present invention provides, for the first time, a practical process for producing useful substances (proteins or peptides especially unstable in *E. coli* cells) by recombinant DNA technique using *E. coli* as a host, utilizing the protease inhibitor produced by T4 phage.

EXAMPLES

Production of human cardiac ventricular myosin L chain being extremely sensitive to *E. coli* protease is shown as examples.

In the examples, purification of DNA, cleavage with restriction enzymes, phosphorylation with T4 polynucleotide kinase, ligation of DNA with T4 DNA ligase and transformation of *E. coli* were all performed according to the methods described in "Molecular Cloning" [edited by Maniatis et al., Cold Spring Harbor, Cold Spring Harbor Laboratory, New York (1982)]. Various restriction enzymes, T4 polynucleotide kinase and T4 DNA ligase, and cloning vectors pUC18 and pBR322 were all commercially obtained from Takara Shuzo Co., Ltd.

(1) Preparation Of Human Cardiac Ventricular Myosin L Chain Open Reading Frame (ORF)

After the cleavage of plasmid pDR-VLC4 DNA containing cDNA encoding human cardiac ventricular myosin L chain (cf. Japanese Patent Application Laid-Open No. 1-240197) with restriction enzyme BamHI, a 640 bp DNA fragment encoding human cardiac ventricular myosin L chain ORF was isolated and purified by agarose gel electrophoresis. This DNA was cleaved with restriction enzyme FokI and the resulting DNA fragments of 201 bp and 389 bp were isolated and purified by gel electrophoresis on 10% polyacrylamide gel, respectively.

In order for the 5'-region of human cardiac ventricular myosin L chain ORF to be ligated in frame to T4 phage uvsY gene, the following two DNAs were synthesized using DNA Synthesizer (manufactured by Pharmacia, Gene Assembler Plus).

(5'-VLC)

5'-GATCCAAAAGCCAGAGCCAAGAAG-
GATGATGCCAAGG-3' (SEQ ID No. 1)

(5'-VLC-R)

5'-GCTGCCTTGGCAT-
CATCCTTCTTGGCTCTGGCTTTTG-3'
(SEQ ID No. 2)

The synthesized two DNAs were phosphorylated at the 5'-ends using T4 polynucleotide kinase. After annealing, the double strand DNA was ligated with the previously obtained DNA fragments of 201 bp and 389 bp using T4 DNA ligase. After the ligation, DNA was recovered by ethanol precipitation and cleaved with restriction enzyme BamHI. The thus obtained human cardiac ventricular myosin L chain ORF DNA of 627 bp was cloned at the BamHI site of cloning vector pUC18, according to the method of Messing et al. [Methods in Enzymology, 101, 20 (1983)] to construct a plasmid pUC-VLC28.

(2) Ligation Of Human Cardiac Ventricular Myosin L Chain ORF With T4 uvsY Gene Promoter After pHTL8 DNA [Takahashi et al., Virology, 120, 122 (1982), pHTL8-inserted *E. coli* C600 strain has been deposited in the Fermentation Research Institute of the Agency of Industrial Science & Technology of Japan (FERM P-8038) as *E. coli* K12 strain TNC101] was cleaved with restriction enzyme HindIII, a 1.4 Kb DNA fragment spanning T4 uvsY gene and gene 25 was isolated and purified by agarose gel electrophoresis. DNA obtained from the cleavage of plasmid pBR322 with restriction enzyme HindIII was ligated with this 1.4 Kb DNA fragment using T4 DNA ligase. *E. coli* C600 (FERM P-8037) was transformed with the resulting DNA.

From the ampicillin-resistant and tetracycline-sensitive transformants, pHB5 in which the 1.4 Kb DNA fragment had been inserted into the HindIII site, was selected.

Plasmid pHB5 carries gene 25 and uvsY gene and has an unique BglII site immediately downstream of uvsY promoter.

Next, pUC-VLC28 DNA was cleaved with restriction enzyme BamHI and a 627 bp DNA fragment was isolated and purified by agarose gel electrophoresis. This 627 bp DNA fragment was ligated with pHB5 previously cleaved with BglII using T4 DNA ligase. *E. coli* MC1061 [Casadaban and Cohen, J. Mol. Biol., 138, 179 (1980)] was transformed with the resulting reaction solution. From the obtained ampicillin-resistant transformants, a plasmid pHB-VLC28 was selected.

In pHB-VLC28, human cardiac ventricular myosin L chain ORF has been inserted downstream of T4 uvsY promoter along with the direction of transcription and its amino acid sequence is somewhat different from the original one. In detail, the second alanine from the N-end has been substituted with 4 amino acids (arginine-leucine-glutamic acid-aspartic acid). (SEQ ID No. 3).

(3) Expression And Induction Of Human Cardiac Ventricular Myosin L Chain By T4dC Phage Infection

*E. coli* MC1061 carrying pHB-VLC28 (FERM BP-3206) was cultured at 37° C. in 100 ml of M9CA medium [0.18% $NaH_2PO_4 \cdot 12H_2O$, 0.3% NaCl, 0.05% $NH_4Cl$, 0.5% glucose, 0.5% Casamino acid (Difco Co.), 1 mM $MgSO_4$ (pH 7.2)] supplemented with 30 μg/ml of ampicillin. At the point when the density reached at $2 \times 10^8$ cells/ml, T4dC phage GT7 (denB−, alc−) [Wilson et al., Nature, 280, 80 (1979)] was infected at m.o.i. of 0.1. After the infection, incubation was continued at 37° C. for further 3 hours and the culture broth was centrifuged at 8000×g for 10 minutes to collect the cells. The resulting cells were suspended in 10 ml of buffer [50 mM Tris-hydrochloride buffer (pH 7.8) containing 20 mM EDTA, 1 mM phenylmethanesulfonyl fluoride (PMSF) and 50 μM 2-mercaptoethanol]. The suspension was homogenized by ultrasonic oscillation to lyze the cells.

Next, centrifugation was carried out at 10000 ×g for 10 minutes to remove the cell debris. Using the supernatant fraction as a sample, human cardiac ventricular myosin L chain was quantitatively determined according to the method of Yazaki et al. (Japanese Patent Application Laid-Open No. 61-286752). Furthermore, the protein concentration in the sample was determined using Protein Assay Kit (manufactured by Bio-Rad Laboratories). For control, human cardiac ventricular myosin L chain was produced in the expression system (Japanese Patent Application Laid-Open No. 1-240197) using tac promoter [Boer et al., Proc. Natl. Acad. USA, 80, 21 (1983)].

The results are shown in Table 1.

TABLE 1

| Bacteria/Plasmid | Expression Induction | Myosin L Chain[3] |
|---|---|---|
| Control: | | |
| MC1061/pDR-VLC4[1] | IPTG (−)[2] | 0.11 |
| MC1061/pDR-VLC4 | IPTG (+) | 0.28 |
| This Invention: | | |
| MC1061/pHB-VLC28 | phage infection | 0.14 |

TABLE 1-continued

| Bacteria/Plasmid | Expression Induction | Myosin L Chain[3] |
|---|---|---|
| MC1061/pHB-VLC28 | (−) phage infection (+) | 11.82 |

[1] Japanese Patent Application Laid-Open No. 1-240197
[2] For expression and induction of tac promoter, 1 mM isopropyl-β-D-thiogalactopyranoside was supplemented.
[3] μg/mg protein As shown in Table 1, human cardiac ventricular myosin L chain was extremely unstable in *E. coli* cells so that is productivity was as low as 0.28 μg/mg protein in the conventional method. On the other hand, in the expression system of the present invention, human cardiac ventricular myosin L chain had the productivity of about 12 μg/mg protein due to the phage infection.

Where a wild type T4 phage, which fell under denB+ strain, was used for the infection instead of T4dC phage GT7, any enhanced production as achieved in the present system was not recognized at all.

Next, T4dC phage GT7 was used for the infection at a variety of m.o.i., using M9CA medium to analyze the productivity of human cardiac ventricular myosin L chain. Table 2 shows the amount of myosin L chain produced per medium at 3 hours after the phage infection.

TABLE 2

| m.o.i. | Myosin L Chain* |
|---|---|
| 0 | 0.02 |
| 0.01 | 0.06 |
| 0.05 | 3.00 |
| 0.10 | 3.70 |
| 0.50 | 3.88 |
| 1.00 | 4.44 |
| 5.00 | 0.15 |

*μg/ml medium

As shown in Table 2, at high m.o.i. infection (e.g., m.o.i.=5.00), lysis occurs immediately after the infection and the productivity was extremely poor as compared to the system at low m.o.i.

Further analysis on the medium used as well as the productivity indicates that the productivity of 15 μg/ml medium was obtained in 2×TY medium (supra) at 6 hours after the infection.

As shown above, the present invention makes it possible to produce the foreign protein in a large quantity in *E. coli*, utilizing the substance productivity of T4 phage, in particular, host protease inhibitor productivity.

*E. coli* MC1061 carrying pHB-VLC28 was deposited in the Fermentation Research Institute of the Agency of Industrial Science & Technology of Japan on Jan. 19, 1990 and given FERM P-11198 as an Accession Number. Thereafter, the deposition was transferred to an international deposition under the Budapest Treaty on Dec. 17, 1990, and given FERM BP-3206 as an Acession Number. T4dC phage GT7 can be prepared from T4 phage (ATCC 11303-B4) in a conventional manner [Snyder, et al., Proc. Natl. Acad. Sci. (USA), 73, 2098 (1976), Wilson, et al., Nature, 280, 80 (1979)].

What is claimed is:

1. A process for producing a foreign protein in *Escherichia coli* comprising the steps of:
   (A) ligating operably a DNA fragment encoding the foreign protein downstream of a transcription initiation signal and a translation initiation signal both derived from a uvsY promoter of a T4 phage and inserting the resulting DNA fragment into a plasmid replicable in *E. coli* to construct a hybrid plasmid;
   (B) transforming *E. coli* with the hybrid plasmid obtained in step (A);
   (C) proliferating the transformant obtained in step (B) in a medium in which said transformant can proliferate and infecting the transformant with T4dC phage at a multiplicity of infection of 0.01 to 1;
   (D) culturing the phage-infected transformant obtained in step (C) to express the foreign protein; and,
   (E) recovering the cultured transformants in step (D) to harvest the desired foreign protein.

2. A process according to claim 1, wherein the transformant is infected with T4dC phage at a multiplicity of infection of 0.05 to 1.

3. A process according to claim 1, wherein the foreign protein is highly sensitive to a protease in *E. coli*.

4. A process according to claim 3, wherein the foreign protein is a human cardiac myosin.

5. A process according to claim 3, wherein the foreign protein is a human cardiac myosin light chain.

* * * * *